United States Patent [19]
Cox et al.

[11] Patent Number: 5,579,765
[45] Date of Patent: Dec. 3, 1996

[54] MONITOR TO DETECT BLEEDING

[76] Inventors: Danny L. Cox, 2616 E. Hills Dr., Moore, Okla. 73160; Bradley J. Bush, 717 Highway Pky., Norman, Okla. 73069

[21] Appl. No.: 452,987

[22] Filed: May 30, 1995

[51] Int. Cl.⁶ ..................................................... A61B 5/00
[52] U.S. Cl. ........................ 128/638; 128/630; 128/734
[58] Field of Search ................................ 128/630, 638–39, 128/734

[56] References Cited

U.S. PATENT DOCUMENTS

| | | | |
|---|---|---|---|
| 2,258,554 | 10/1941 | Heyer et al. | 200/52 |
| 3,245,068 | 4/1966 | Wegryn et al. | 340/235 |
| 3,832,993 | 9/1974 | Clipp | |
| 4,193,068 | 3/1980 | Ziccardi | 340/604 |
| 4,583,546 | 4/1986 | Garde | 128/638 |
| 5,036,859 | 8/1991 | Brown | 128/638 X |
| 5,050,735 | 9/1991 | Levy | 128/630 X |

*Primary Examiner*—Angela D. Sykes
*Assistant Examiner*—Ryan Carter
*Attorney, Agent, or Firm*—Molly D. McKay, P.C.

[57] ABSTRACT

A monitor for detecting external bleeding from a puncture site on a patient. The monitor is provided with a self-sticking bandage portion on one end connected by means of a flexible connecting strip to a self-sticking holder portion on an opposite end. The bandage portion is applied so the puncture site is visible through a transparent window provided over a central opening in the bandage portion. A pair of spaced apart wires encircles the central opening, extends across the connecting strip and removably secures to a portable alarm device containing a battery and alarm connected in series by means of the wires. When the puncture site hemorrhages, blood contacts the wires, allowing electrical current to flow between the wires via the electrically conductive blood and thus supplying electricity to the alarm in order to activate it.

12 Claims, 3 Drawing Sheets

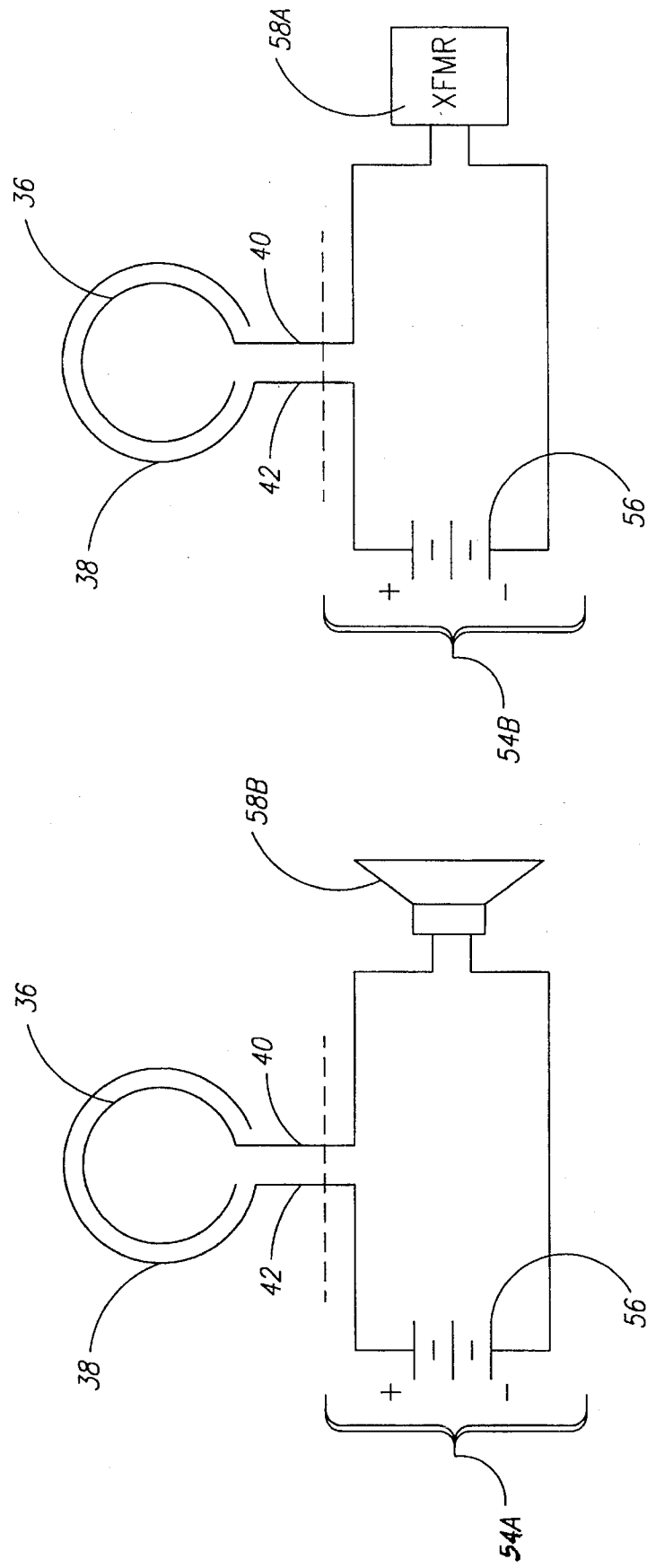

MONITOR TO DETECT BLEEDING

BACKGROUND OF THE INVENTION

1. Field of the Invention

The present invention relates to a disposable bandage designed to quickly detect and alert medical personnel of external bleeding in post angioplasty patients. More specifically, the present invention relates to a bandage within which is provided an open D.C. circuit capable of being closed by the patient's blood in order to activate an alarm.

2. Description of the Related Art

A variety of medical procedures involve puncturing of a large artery. Some of these procedures are Cardiac Catheterization (also known as Left Heart Catheterization, LHC, Coronary Angiography, or Coronary Arteriogram), Percutaneous Transluminal Angioplasty (also known as PTA), Percutaneous Transluminal Coronary Angioplasty (also known as PTCA), Percutaneous Coronary Atherectomy, Directional Atherectomy, Percutaneous Transluminal Coronary Rotoblator, Stents (including Renal, Biliary and Intracoronary Stents), and Electrophysiology Studies.

Typically the artery involved is either the Right or Left Femoral Artery. When the Femoral Arteries are not available, usually due to blockage, either the Left or Right Brachial Artery is normally used.

Generally, these procedures are done in order to increase blood flow in the body where the flow has become restricted due to the gradual buildup of plaque in the arteries.

The procedure is started by identifying the artery to be used. Then the site is shaved, cleaned, and an anesthetic agent is used to numb the area. A small scalpel blade is then used to make an incision through the skin. This allows access through the "tougher" layers of the skin. Then a large "needle" with a plastic sheath or tube (much like a large Intravenous Catheter) approximately six inches long (Atherectomy sheaths can be as long as 18 inches) is advanced into the chosen artery. When this is accomplished, the "needle" is removed from the sheath. This gives the doctor easy access from outside the body to the interior of the artery. Again, this is much like the process used when placing an IV catheter except for the much larger size of the "needle" and sheath. The sheath is also known as an Introducer, because the doctor is allowed to "introduce" wires into the artery via the sheath. The sheath is provided with a plug which prevents blood from flowing outside the patient's body, but through which specially designed wires can be inserted into and removed from the artery.

Once this is accomplished, the doctor is then able to thread a catheterization wire through the sheath, into the artery and into the coronary arteries. This wire is extremely small, typically a couple of millimeters in diameter. With this device, the doctor is able to inject a radiopaque dye into the coronary arteries. He may also inject dye into other arteries, if he chooses, by merely manipulating the wire to other parts of the body, for example, the renal arteries, biliary arteries, the aorta, the femoral arteries, or the carotid arteries.

If blockage of an artery is detected, the doctor may opt to intervene using one of the various methods available. All these methods are accomplished via special wires like the cardiac catheterization wires. Each special wire has unique fittings that accomplish the same goal, which is increasing blood flow, but each accomplishes this goal in a slightly different manner. The details of these different methods will not be reviewed herein since they are commonly known in the medical profession. Anticoagulants are administered to the patient when certain of these methods are employed in order to prevent undesirable blood clotting within the arteries.

Once the procedure is completed, the wire with its particular application end is removed from the body via the sheath. This leaves the patient with only a sheath in the artery again, at the puncture site. For patients that did not receive anticoagulants, the sheath is generally removed immediately after the procedure, pressure is held and then the patient recovers after a specified number of hours of bed rest. If the patient received anticoagulants after any procedure, the effect of the anticoagulant must be allowed to lessen before the sheath/introducer is removed, pressure is applied and the patient is then required to remain on bed rest for a specified number of hours while he recovers.

Nursing care during this period of bed rest involves visual and tactile assessment of the puncture site. These assessments occur quite frequently at first, generally about every 15 minutes, and occur less frequently during the course of the patient's care, ending with assessments occurring as infrequently as two hours apart.

In addition to the visual and tactile assessments, most patients are also monitored continuously during this period of time with an electrocardiograph (ECG), either at the bedside or via a remote system. However, if the patient were to begin hemorrhaging from the puncture site, substantial loss of blood generally occurs before the ECG registers any significant and noticeable changes which would alert the nursing staff of a problem. If the patient is asleep when his puncture site begins to bleed, and therefore, unable to call the nursing staff for help, substantial loss of blood can occur before the bleeding is detected.

Currently, there is no means, other than depending on the patient to call the nurses when he begins to bleed, for detecting this type of bleeding early enough to prevent the patient from losing a large volume of blood.

The present invention addresses this need by providing a disposable bandage which is applied over the puncture site and which is equipped with electrical means for detecting bleeding and activating an alarm when bleeding is detected. The present invention is provided with a clear observation window which allows visual and tactile assessment of the puncture site without removing the invention from the patient. The invention is also provided with a flexible segment which connects that portion of the invention which covers the puncture site and another portion of the invention which holds the power source and alarm mechanism. This flexible segment allows the two connected portions to be positioned on the patient's skin in order to allow the patient to be mobile without dislodging or disconnecting the invention.

SUMMARY OF THE INVENTION

The present invention is a monitor for detecting external bleeding on a patient. The monitor has two self-sticking portions, a bandage portion and a holder portion, which attach to the patient by means of a self-sticking backing provided on an underside of each of the portions. The two portions are connected by a flexible connecting strip which serves as a flexible bridge for two wires which each run between the two portions. The bandage portion is provided with a gauze layer which lies against the patient so the gauze layer is between the patient and a first coiled end of each wire. The bandage portion and the gauze layer are provided respectively with a bandage opening and gauze opening so that the two openings coincide with each other. A transparent window seals the openings so that a puncture site on the patient can be observed therethrough.

A second connecting end provided on each wire removably connects to a portable alarm device secured within a pocket provided on the holder portion. The portable alarm device contains a power source, preferably a 9-volt battery, and an alarm comprised of either an audible alarm or a transmitter for remotely producing a signal to alert medical personnel. The power source and alarm are connected together and with the wires to form a normally open electrical series circuit. If bleeding occurs, the electrically conductive blood completes the circuit where it is open between the first coiled ends, thereby supplying electricity to the alarm to activate it.

BRIEF DESCRIPTION OF THE DRAWINGS

FIG. 4 is a schematic diagram illustrating the electrical arrangement of the two wires, the battery and the alarm of a preferred embodiment of the present invention where the alarm is an audible type alarm.

FIG. 5 is a schematic diagram illustrating an alternate electrical arrangement of the two wires, the battery and the alarm where the alarm is a transmitter which activates a signal remotely.

DETAILED DESCRIPTION OF THE PREFERRED EMBODIMENT

Figure 1:
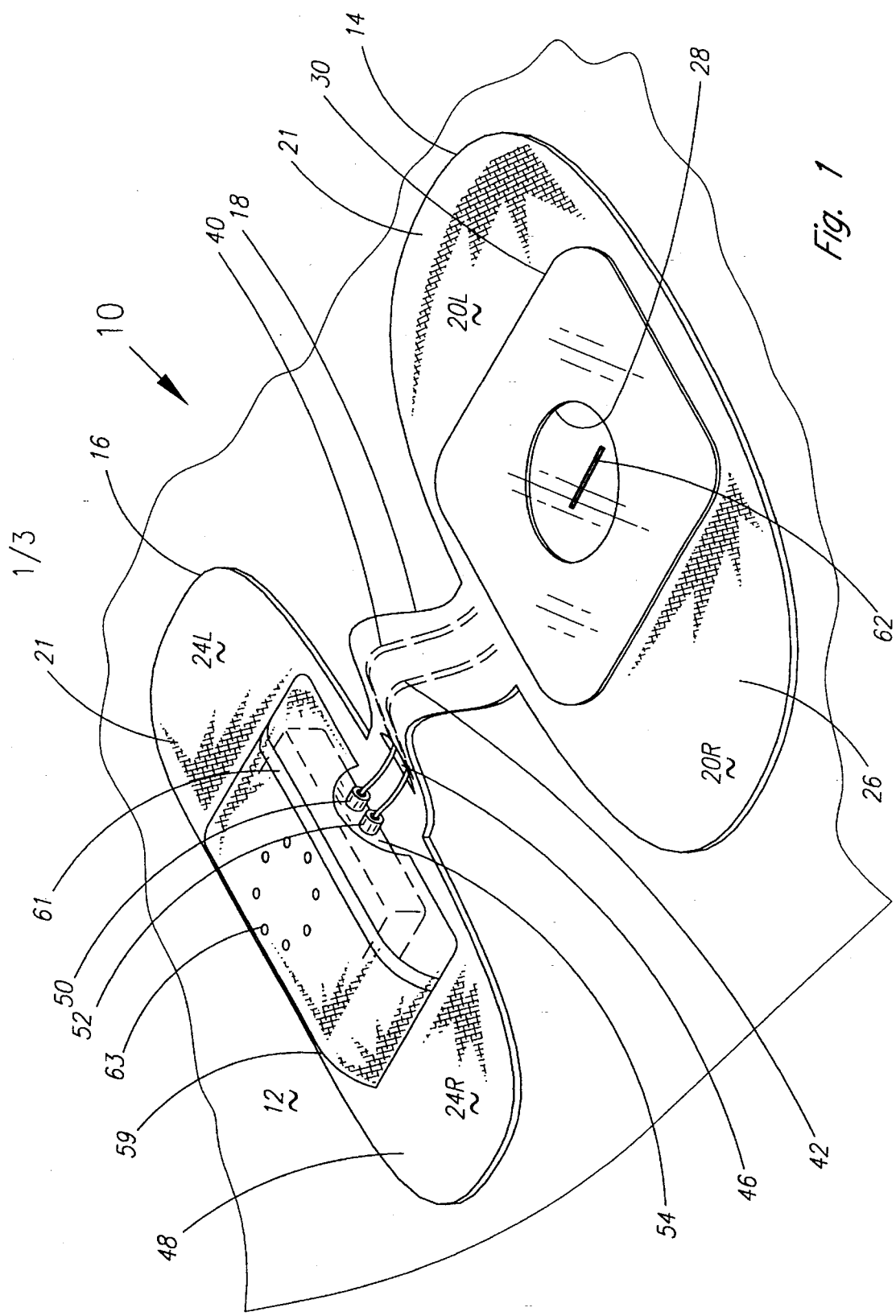
FIG. 1 is a perspective view of a monitor to detect bleeding constructed in accordance with a preferred embodiment of the present invention as it would appear in use on a patient.
Figure 2:
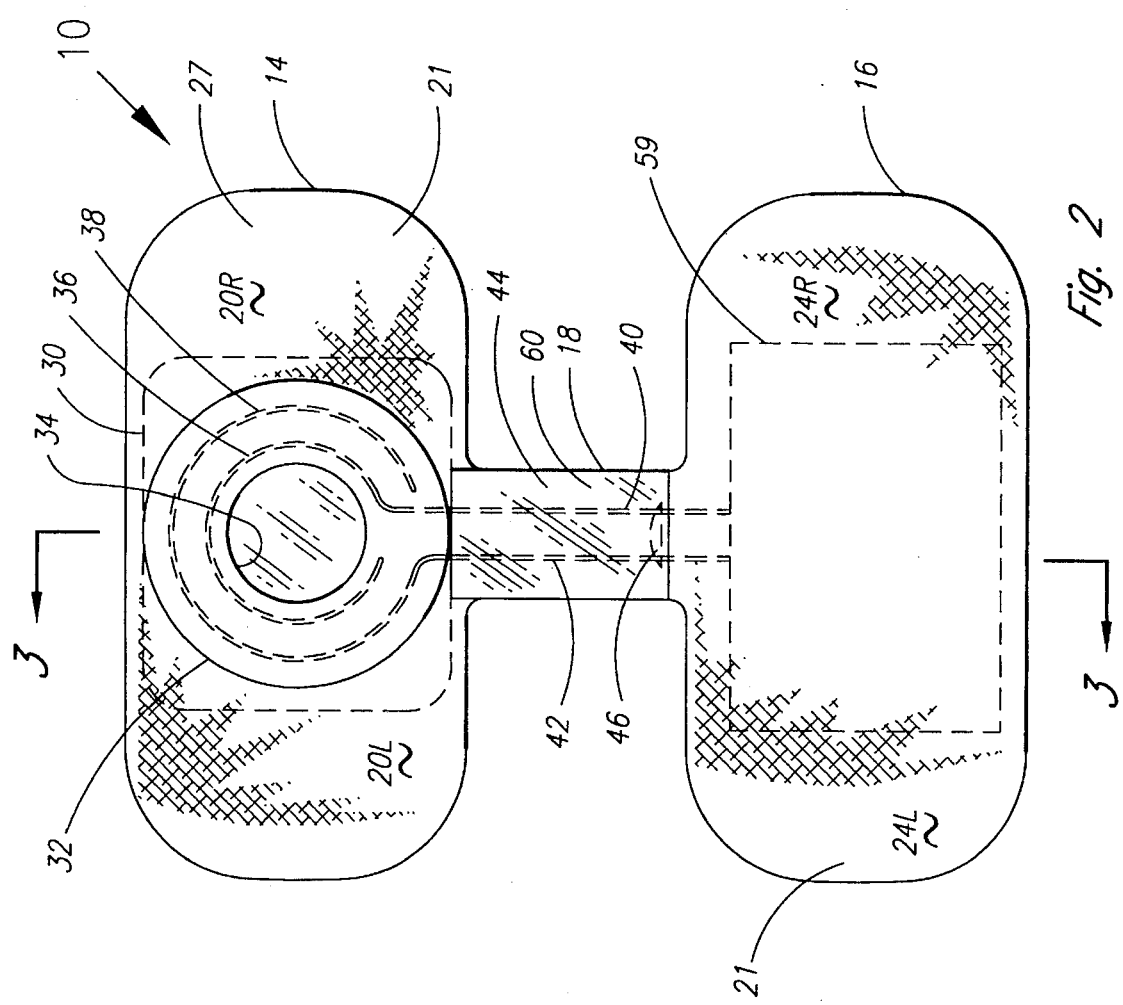
FIG. 2 is a bottom plan view of the invention of FIG. 1 with the backing layer removed from the connecting strip in order to reveal the wires.

Referring now to the drawings and initially to FIGS. 1 and 2, there is illustrated a monitor 10 for detecting bleeding in a post-angioplasty patient 12. Although use of the monitor 10 is described for use on a post-angioplasty patient 12, it is contemplated that the monitor 10 could be employed with any patient having wounds, particularly those involving arterial invasion, which need to be closely monitored for bleeding. As shown in FIG. 1, the monitor 10 consists of a bandage portion 14 and an opposite holder portion 16 which connect together by means of a flexible connecting strip 18, as will be explained more fully hereafter.

The bandage portion 14 is provided with outwardly extending left and right bandage wings 20L and 20R formed of a flexible material 21 which is provided with self-sticking adhesive on an underside 22 of the flexible material 21, such as the plastic type of material used for commercially available adhesive bandages. The holder portion 16 is also provided with outwardly extending left and right holder wings 24L and 24R formed of the flexible material 21 which has a self-sticking adhesive on its underside 22. Likewise, the connecting strip is formed of the flexible material 21 whose underside 22 is provided with a self-sticking adhesive. In fact, as illustrated in the preferred embodiment of the invention shown in FIGS. 2 and 3, the bandage portion 14, the holder portion 16, and the connecting strip 18 are all formed from a continuous piece of the flexible material 21 which has self-sticking adhesive on its underside 22.

Referring now to FIG. 1, the material 21 forms a top surface 26 of the bandage portion 14 and its underside 22 forms a bottom surface 27 of the bandage portion 14. The bandage portion 14 is provided with a central bandage opening 28. A clear observation window 30 is provided attached to the bandage portion 14 so that the window 30 completely covers and seals the central bandage opening 28.

A gauze layer 32 which is somewhat smaller than the bandage portion 14 and is provided with a central gauze opening 34 which coincides with the central bandage opening 28, is attached on the bottom surface 27 of the bandage portion 14. The gauze layer fully encircles the bandage opening in order to protect the patient 12 from contact with coiled ends 36 and 38 of first and second electrical wires 40 and 42 which are provided concentrically around the central bandage opening 28 and located between the gauze layer 32 and the bottom surface 27 as will be more fully explained hereafter.

The coiled ends 36 and 38 are spaced apart from each other, with the first coiled end 36 located between the central bandage opening 28 and the second coiled end 38. Neither of the coiled ends 36 and 38 contacts its respective wire 40 or 42 or the wire 42 or 40 of the other coiled end 38 or 36.

The wires 40 and 42 extend from their respective coiled ends 36 and 38, parallel with one another along a bottom surface 44 of the connecting strip 18, through a strip opening 46 provided in the connecting strip 18 adjacent the holder portion 16 to a top surface 48 of the holder portion 16. Each of wires 40 and 42 is provided with a connecting end, 50 and 52 respectively, located on the top surface 48 of the holder portion 16. Each of the connecting ends 50 and 52 are removably connectable to a portable alarm device 54. A variety of different types of portable alarm devices 54 may be used for this purpose. As illustrated in FIGS. 4 and 5, each such portable alarm device 54 will be provided with a battery power supply 56, preferably a 9-volt battery, connected in series with the two wires 40 and 42 via their connecting ends 50 and 52 and also connected in series with an alarm 58. Everything in FIGS. 4 and 5 below the broken lines is included within the portable alarm device 54. As illustrated in FIG. 5, the portable alarm device 54A may have as its alarm 58 a transmitter device 58A for remotely alerting the nursing staff of a problem or, as shown in FIG. 4, the portable alarm device 54B may have as its alarm 58 an audio alarm 58B, such as a piezo-type pulsating alarm, designed to produce a loud warning siren. The wires 40 and 42 form a normally open electrical circuit between the power supply 56 and the alarm 58.

The top surface 48 of the holder portion 16 is provided with a pocket 59 which holds the portable alarm device 54 against the top surface 48, even when the patient 12 moves around. In order to prevent the portable alarm device 54 from slipping out of the pocket 59, the pocket 59 is provided with a pocket closure 61 which serves to close the pocket 59, preventing the portable alarm device 54 from coming out of the pocket 59 until the pocket closure 61 is reopened. The pocket closure 61 may be any type of closure capable of being sealed and reopened. The pocket 59 is preferably provided with pocket openings 63 therethrough so that sound from an audio alarm 58B can easily be heard by the patient 12.

Figure 3:
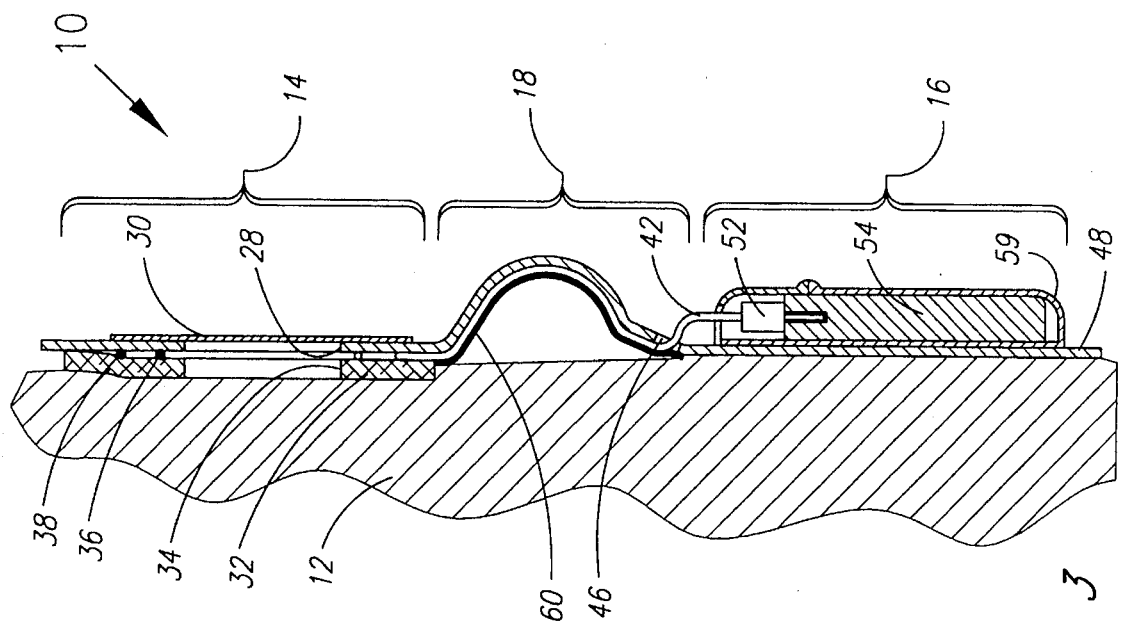
FIG. 3 is a cross-sectional view taken along line 3—3 of FIG. 2.

The bottom surface 44 of the connecting strip 18 is provided with a backing layer 60 which extends from the gauze layer 32 to preferably slightly beyond the strip opening 46. The wires 40 and 42 are located between the bottom surface 44 and the backing layer 60, with the bottom surface 44 serving to shield the patient 12 from contact with the wires 40 and 42, as can be seen in FIG. 3.

As illustrated in FIG. 1, in order to use the monitor 10, the bandage portion 14 is attached to the patient 12 via its self-sticking bottom surface 24 so that a puncture site 62 resulting from a previously performed angioplasty or other similar medical procedure is centered in and visible through the transparent window 30. The holder portion 16 is then attached to the patient 12 via its self-sticking bottom surface 64 so that the connecting strip 18 is flexed upward, as shown in FIGS. 1 and 3. The purpose for having the connecting strip 18 flexed upward is to allow enough slack in the connecting strip 18 so that the bandage and holder portions 14 and 16 do not bind when the patient 12 moves around and so that the wires 40 and 42 are not thereby pulled out of electrical connection from the portable alarm device 54.

Once the monitor 10 has been properly attached to the patient 12, the gauze layer 32 serves to prevent perspiration of the patient 12 from reaching the coiled ends 36 and 38 of wires 40 and 42.

Both perspiration and blood are electrically conductive liquids, and if either is allowed to saturate the gauze layer 32 and reach the spaced apart coiled ends 36 and 38, this thereby completes or, forms an electrically closed circuit of the normally open electrical circuit existing between the battery power supply 56 and the alarm 58, thus causing the alarm 58 to activate.

If the patient 12 begins to hemorrhage from the puncture site 62, blood quickly completes the circuit between the coiled ends 36 and 38, thus causing the alarm 58 to activate. The activation of the alarm 58 immediately signals medical personnel that bleeding is occurring. Upon receiving the signal from the alarm 58, medical personnel can take quick action to stop the bleeding, generally by again applying direct pressure to the puncture site 62 in order to cause a clot to form.

At that point, the old monitor 10 is removed, the battery supply is removed for reuse, the old monitor 10 is properly discarded and a clean new monitor 10 is attached to the patient 12, as previously described.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A monitor for detecting bleeding comprising:

a bandage portion securable over a puncture site on a patient, said bandage portion being provided with a central bandage opening therethrough, and two spaced apart electrically conductive wires encircling said central bandage opening, each of said wires being electrically connected in series with a power supply and an alarm.

2. A monitor according to claim 1 further comprising:

a transparent window provided in said central bandage opening.

3. A monitor according to claim 1 wherein said wires are removably connected to a portable alarm device which is comprised of electrically connected said power supply and said alarm.

4. A monitor according to claim 3 wherein said power supply is a battery.

5. A monitor according to claim 1 further comprising:

a holder portion secured by means of a flexible connecting strip to said bandage portion, said wires each extending from said bandage portion across said connecting strip to said holder portion, holding means being provided on said holder portion for holding said power supply and said alarm.

6. A monitor according to claim 5 wherein both said holder portion and said bandage portion are provided with self-sticking bottom surfaces.

7. A monitor according to claim 1 further comprising:

a gauze layer being provided on a bottom surface of said bandage portion so that said gauze layer lies between the patient and said wires.

8. A monitor according to claim 7 further comprising:

said gauze layer being provided with a central gauze opening, said central gauze opening coinciding with said central bandage opening.

9. A disposable bandage for monitoring for bleeding from a puncture site of a post-angioplasty patient comprising:

a bandage portion securable over a puncture site on a patient, said bandage portion being provided with a central bandage opening therethrough, two spaced apart concentrically arranged electrical conductors encircling said bandage opening, a first end of each two spaced apart concentrically arranged electrical conductors removably secured around the puncture site on the patient, an opposite end of each said two electrical conductors being electrically connected in series with a power source and an alarm.

10. A bandage according to claim 9 further comprising:

said first ends of said electrical conductors being secured to said patient by means of the bandage portion, said bandage portion being provided with a transparent window covering the central bandage opening in said bandage portion so that the puncture site may be observed therethrough, said first ends being concentrically arranged around said bandage opening.

11. A bandage according to claim 10 wherein said power source and said alarm are removably connected to said electrical conductors.

12. A bandage according to claim 11 further comprising:

a holder portion attached to said bandage portion by means of a flexible connecting strip, said holder portion securable to said patient, and a holding means provided on said holder portion in order to secure said power source and said alarm to said holder portion.

* * * * *